United States Patent [19]

Burgaud

[11] Patent Number: 5,458,848
[45] Date of Patent: Oct. 17, 1995

[54] METHOD OF DEODORIZING A FORMULATION CONTAINING AT LEAST ONE COMPOUND BEARING A THIOL GROUP AND DEODORIZED FORMULATION THUS OBTAINED

[75] Inventor: Hervé Burgaud, Dammartin en Goele, France

[73] Assignee: L'Oreal, Paris, France

[21] Appl. No.: 235,462

[22] Filed: Apr. 29, 1994

[30] Foreign Application Priority Data

Apr. 30, 1993 [FR] France .................................. 93 05154

[51] Int. Cl.⁶ .................................................... A61L 9/00
[52] U.S. Cl. ................................. 422/5; 422/1; 422/122; 210/638; 210/644
[58] Field of Search ..................... 422/1, 5, 120, 422/122, 211, 238, 239, 261, 262; 210/638, 644, 651, 502.1; 132/202, 203, 204, 209

[56] References Cited

U.S. PATENT DOCUMENTS

| | | | |
|---|---|---|---|
| 4,840,812 | 6/1989 | Tominaga | 426/488 |
| 5,183,656 | 2/1993 | Uesaka et al. | 424/76.1 |
| 5,184,630 | 2/1993 | Jung | 132/202 |
| 5,234,884 | 8/1993 | Mouri et al. | 422/5 X |

FOREIGN PATENT DOCUMENTS

| | | |
|---|---|---|
| 0488665 | 6/1992 | European Pat. Off. . |
| 2148022 | 3/1973 | France . |
| 2606027 | 5/1988 | France . |
| 2679448 | 1/1993 | France . |
| 9301791 | 2/1993 | WIPO . |

OTHER PUBLICATIONS

Tanimura Teruo, "Cold Wave Treating Method", Patent Abstract of Japan, vol. 6, No. 261 (C–141), Dec. 1982.
Nakayama Jiyunichi, "Deodorization of Thioglycolic Acid or its Salt", Patent Abstract of Japan, vol. 8, No. 114 (C–225) May 1984.

Primary Examiner—Robert J. Warden
Assistant Examiner—Krisanne M. Thronton
Attorney, Agent, or Firm—Cushman Darby & Cushman

[57] ABSTRACT

Method of deodorizing in order to remove malodorous compounds which are present in or formed from a liquid formulation containing at least one compound bearing a thiol functional group, of formula:

$$HS-A-Y-B \qquad (I)$$

in which:

1) the liquid formulation is placed in contact with an inert membrane which is permeable to the malodorous compounds and impermeable to the compound(s) of formula (I); and 2) the malodorous compounds which have passed through the membrane are placed in contact with at least one chemical substance reacting with the said malodorous compounds and/or with at least one physical adsorption substance having a large specific surface area which binds the said malodorous compounds.

8 Claims, 1 Drawing Sheet

METHOD OF DEODORIZING A FORMULATION CONTAINING AT LEAST ONE COMPOUND BEARING A THIOL GROUP AND DEODORIZED FORMULATION THUS OBTAINED

The present invention relates to a method of deodorizing a formulation containing at least one compound bearing a thiol functional group (—SH) and the deodorized formulation thus obtained.

Organic compounds bearing thiol functional group(s) are well known compounds, which have increasingly numerous applications. One of these applications is the permanent deformation (curling and uncurling) of hair, which consists, in a first step, in opening disulphide linkages (S—S) of the cystine units of keratin using a composition containing at least one thiol functional group-bearing organic compound acting as a reducing agent (reduction step), which makes it possible to impart the desired shape to the hair; then, after having rinsed the head of hair, in reforming, in a second step, the said disulphide linkages by applying an oxidizing composition to the hair (oxidation step, also known as setting step), in order to set the hair in the shape which has been given to it; with this aim, thioglycolic acid, thiolactic acid or their mixtures, or alternatively the esters of these acids, for example the glycerol or glycol monothioglycolates, or also cysteine or cysteamine are particularly used. Thioglycolic or thiolactic acids and their salts are also used in hair-removing milks and creams. Thioglycolic and thiolactic acids, as well as cysteine, are also employed as intermediate products in the manufacture of pharmaceutical products.

Unfortunately, if, in general, the compounds bearing a thiol functional group have, in the pure state, an odor which is not unpleasant, they still contain, in practice, sulphur compounds such as hydrogen sulphide and low molecular weight mercaptans, in particular methane-thiol or ethanethiol, which have a particularly unpleasant, nauseating odor. Only very low quantities of these sulphur compounds are required for their presence to be detected by odor, the nose being, in this case, the best instrument of detection. In the ensuing description and in the claims, these sulphur compounds will be denoted by the term "malodorous compounds".

The presence of these malodorous compounds is linked to various poorly understood processes of decomposition of the compounds bearing a thiol group, in particular by oxidation. Formation of these malodorous compounds may be followed in the course of time by various analytical techniques, in particular by the so-called "head space" method in gas chromatography which is, for example, described in "Applied Headspace Gas Chromatography, B. Kolb, Editions Heyden, 1980".

In the various applications of the compounds bearing a thiol functional group, and more particularly in their cosmetic applications, the odor given off by the products used constitutes a real nuisance for the users. It has been attempted to mask the odor by perfumes, but the odor is generally too powerful to be able to be masked significantly.

It has thus been sought to remove the malodorous compounds. With this aim, it has already been proposed, in the Japanese Patent Application published under the No. 84-027,866, to deodorize thioglycolic acid, pure or in aqueous solution, by extraction using a $C_4$–$C_8$ non-aromatic hydrocarbon. Given that it is necessary to use an installation of relatively large capacity in order to carry out the extraction, it is practically impossible to deodorize the thiol functional group-bearing compounds just before their use, such that their storage is, in practice, obligatory. Now, it has been observed that, if this method makes it possible to obtain a deodorized acid, the deodorizing effect obtained is not long-lasting because the malodorous compounds form again during storage, particularly in the presence of oxygen, and even, in certain cases, the odor returns at a higher level than the initial level.

It is thus necessary to find a method of removing the malodorous compounds which makes it possible to carry out this removal progressively as the said compounds are formed in order to have, at the time of use, a compound bearing at least one thiol functional group, which is deodorized even after a prolonged storage.

It is known to remove, in gases, the malodorous compounds in question using substances which react with the said malodorous compounds, giving compounds which are of inoffensive odor. These compounds, as described in the Japanese Patent Application published under the No. 88-264,139, may be silver oxides, optionally mixed with Co, Mn or Cu oxides. These chemical substances may, in a known manner, be contained in a semi-permeable membrane through which the gaseous stream to be purified passes; for example, the Japanese Patent Application published under the No. 88-023,708 describes the use of a porous membrane impregnated with a metal phthalocyanine complex and treated with copper nitrate.

Moreover, it is known from FR-A 2,152,829, to decontaminate a stream of air by passing the gas through a structure consisting of two semi-permeable membranes, that is to say permeable to the gases and to vapors but impermeable to liquids, the space between the two semi-permeable membranes containing an agent which is capable of reacting with the contaminant. According to this document, the semi-permeable membrane thus serves essentially to keep the agent capable of reacting with the contaminant in place and to prevent it from being entrained by the air. In addition, the air contains no active derivatives bearing thiol functional group(s), which would not be desired to react with the contaminant-retaining agent; there is thus no need to separate two thiol derivatives.

BACKGROUND OF THE INVENTION

According to the present invention, a method has been found for deodorizing thiol group-bearing compound(s), which method makes it possible selectively to remove the malodorous compounds without the reactants used to remove the said malodorous compounds having an action on the treated thiol group-bearing compound(s); according to this method, a system is used which is in contact with the said thiol group-bearing compound in liquid form, that is to say in the form of a pure liquid or in the form of a solution.

Figure 1:
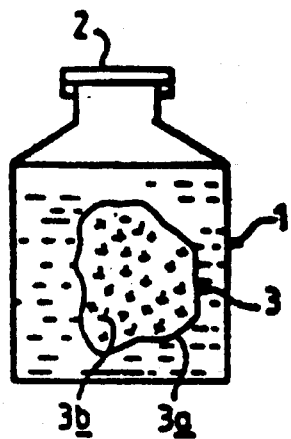
FIG. 1 is a schematic illustration of an assembly.

The subject of the present invention is thus a method of deodorizing in order to remove the malodorous compounds which are present in or formed from a liquid formulation containing at least one compound bearing a thiol functional group, of formula:

HS—A—Y—B  (I)

in which formula Y represents —COO— or —NH— and a) when Y denotes —COO—:
   A represents:
      the divalent radical: —(CH$_2$)$_n$ where n is 1 or 2
      the divalent radical:

where R represents a linear or branched C$_1$–C$_3$ alkyl radical, and
B represents the radicals —H; —CH$_2$—CH$_2$OH; —CH$_2$—CHOH—CH$_2$OH;

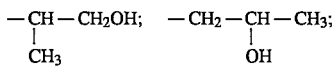

b) when Y represents —NH—
   A represents:

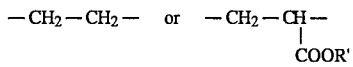

R' representing —H, a methyl radical or an ethyl radical
B represents —H or, when A represents —CH$_2$—CH$_2$—,
B also represents a radical —CO—R",
R" representing a linear or branched C$_1$—C$_4$ alkyl radical; characterized in that:

1) the liquid formulation is placed in contact with an inert membrane which is permeable to the malodorous compounds and impermeable to the compound(s) of formula (I); and 2) the malodorous compounds which have passed through the membrane are placed in contact with at least one chemical substance reacting with the said malodorous compounds and/or with at least one physical adsorption substance having a large specific surface area which binds the said malodorous compounds.

In this method, the membrane thus serves both to separate selectively the malodorous compounds with respect to the compound(s) of formula (I) and to maintain the chemical and/or physical adsorption substances.

The liquid formulation containing at least one compound of formula (I) may contain the compound of formula (I) as it is, if it is in the liquid state under the temperature and pressure conditions applied to the formulation, or the compound of formula (I) in solution form, in particular in aqueous solution form.

The compound of formula (I) is advantageously chosen from the group formed by thioglycolic acid (or mercaptoacetic acid), thiolactic acid (or 2-mercaptopropionic acid), 3-mercaptopropionic acid, glycerol monothioglycolate, glycerol 2-mercaptopropionate, an azeotropic mixture of 2-hydroxypropyl thioglycolate and 2-hydroxy-1-methylethyl thioglycolate (as described in FR-A 2,679,448), cysteamine (or 2-aminoethanethiol) and its N-acylated derivatives, the acyl radical containing 2 to 5 carbon atoms, cysteine and the methyl and ethyl cysteinates. Thioglycolic and thiolactic acids are preferred.

The membrane used according to the invention is advantageously made of a material of hydrophobic nature chosen from the group formed by polytetrafluoroethylene, for example that marketed under the trade name "TEFLON" by the company "DUPONT DE NEMOURS", polyethylene, in particular low density polyethylene, polypropylene, polystyrene and copolymers of butadiene and styrene, in particular that marketed under-the trade name "STYROLUX" by the company "BASF".

The chemical substance(s) reacting with the malodorous compounds is (are) chosen so as to give, by reaction, compounds which no longer have any odor. It (they) may advantageously be chosen from the group formed by a finely divided metal, such as copper, zinc or silver, a finely divided metal oxide such as Cu$_2$O, MnO$_2$, ZnO or silver oxides and a solution, in particular an aqueous solution, of metal salt(s), such as cadmium acetate, lead acetate, copper sulphate or iron sulphate.

The physical adsorption substance for the malodorous compounds is advantageously chosen from the group formed by active charcoals, silica gels, alumina, molecular sieves, styrene-divinylbenzene or styrene-ethenylbenzene copolymers, in particular that marketed under the trade name "PORAPAK" by the company "WATERS", and polyphenylene oxides, in particular that marketed under the trade name "TENAX" by the company "AKZO".

The membrane-chemical substance and/or physical adsorption substance assembly used in the method of the present invention may take various forms.

In a first advantageous embodiment of this assembly, the membrane lines the inner face of the wall of the receptacle containing the formulation to be deodorized; the reacting chemical substance(s) and/or the physical adsorption substance(s) intended to act on the malodorous compounds is (are) then arranged between the membrane and the wall of the said receptacle.

According to a variant of this embodiment, the membrane constitutes the inner face of the wall of a cap intended to cover a head of hair treated with a formulation generating malodorous compounds; the chemical substance(s) and/or physical adsorption substance(s) is (are) arranged between the said membrane and the outer face of the cap. Such a cap allows the unpleasant odors to be avoided during a permanent hair setting because the malodorous components are trapped inside the cap.

Figure 2:
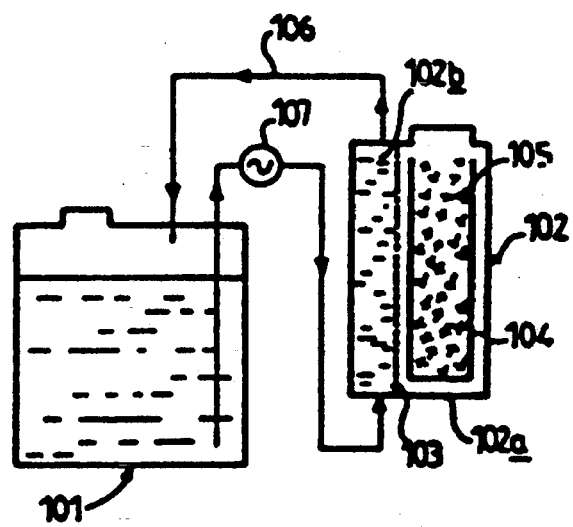
FIG. 2 is a further illustration of a receptacle.

According to a second embodiment, the membrane forms a bag which is filled with chemical substance(s) and/or physical adsorption substance(s) intended to act on the malodorous compounds; one or more of these bags is (are) then immersed in the receptacle in which the liquid formulation to be deodorized is packaged. These bags may have variable shapes, of circular, square or rectangular cross-section; they may consist of tubes which allow the passage of the liquid formulation. An assembly of this type is illustrated schematically in FIG. 1. In this FIG. 2, the receptacle is a bottle denoted by the reference 1; it is sealed in a leaktight manner by a lid 2 and it contains a sachet 3 consisting of a hermetically welded membrane 3a, which contains at least one reacting chemical substance and at least one physical adsorption substance 3b.

According to a third embodiment, the reacting chemical substance(s) and/or the physical adsorption substance(s) is (are) in particulate form and the membrane constitutes a covering around each of the said particles. The particles of coated substance(s) are introduced into the receptacle containing the liquid formulation to be deodorized.

Figure 3:
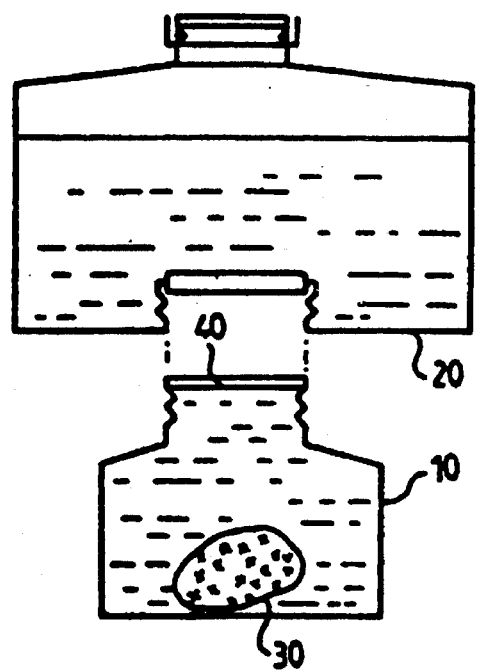
FIG. 3 is yet a schematic of a packing.

According to a fourth embodiment, the membrane, as well as the reacting chemical substance(s) and/or the physical adsorption substance(s), are situated outside the receptacle containing the formulation to be deodorized, and a circulation device makes it possible to place the said liquid formulation in contact with the membrane. An assembly of this type is illustrated schematically in FIG. 2. The installation illustrated in FIG. 3 includes a reservoir 101 containing the liquid formulation to be deodorized and a deodorizing unit 102 separated into two compartments 102a, 102b by a membrane 103. Compartment 102a contains a removable basket 104 containing the reacting chemical substance(s) and/or the physical adsorption substance(s) 105. The other compartment 102b is connected to reservoir 101 via conduits 106, such that the liquid contained in reservoir 101 can circulate in a closed circuit from reservoir 101 to compartment 102b and vice versa; the circulation is effected by a pump 107 which generates a slight excess pressure on the side of the membrane 103 on which compartment 102b is located, by means of which the malodorous compounds pass from compartment 102b to compartment 102a. Reservoir 101 is preferably maintained under inert atmosphere.

According to the invention, the (membrane/reacting chemical substance(s) and/or physical adsorption substance(s)) assembly may be in contact with the compound(s) of formula (I) during the entire storage time. Consequently, this assembly progressively removes the malodorous compounds as they are formed and, at the time of use, the formulation containing the compound(s) of formula (I) is still found in deodorized form.

The subject of the present invention is also the deodorized liquid formulation of compound(s) of formula (I) obtained according to the method described above.

The deodorized formulation of compound(s) of formula (I) may be used in all the industrial applications known for these compounds. The compounds of formula (I) are generally combined with other ingredients in the formulation, depending on the application. The deodorizing efficiency allows them to be used, without giving an unpleasant odor, in any composition which is not required to have an unpleasant odor and in which the other ingredients have no unpleasant odor.

However, particularly when the composition used contains ingredients which are likely to nullify the benefit of the deodorizing by inducing the formation of malodorous compounds, it may be advantageous to package separately the compound(s) of formula (I) and some of the ingredients of the desired final composition; the quantity of composition necessary for the application is then prepared at the last moment. A packaging of this type is illustrated schematically in FIG. 3. The packaging illustrated contains two bottles 10, 20; the first bottle 10 contains a compound of formula (I) and a sachet 30 formed by a hermetically closed membrane containing at least one reacting chemical substance and/or one physical adsorption substance. Bottle 20 contains the other ingredients of the composition to be prepared. Bottle 10 is closed by a lid 40 and a device carried by bottle 20 makes it possible to tear open this lid 40 and to introduce the contents of bottle 10 into bottle 20, in order to prepare the desired composition at the time of use. A system of two bottles which may be used according to the present invention has, for example, been described in EP-A 0,528,707.

The examples below, given by way of illustration and with no limitation being implied, will allow a better understanding of the invention.

DESCRIPTION OF PREFERRED EMBODIMENTS

EXAMPLE 1

A hermetic sachet of low density polyethylene, of 40 µm in thickness and of 50 $cm^2$ surface area, containing 0.5 g of cuprous oxide, were introduced into a 60 ml bottle. 30 ml of an aqueous thioglycolic acid solution at a concentration of 184 g/l (2M) are next introduced. The bottle is closed; after closing it contains 30 ml of air.

An identical bottle, but not containing a deodorizing sachet, is simultaneously prepared.

The two bottles are stored at ordinary temperature and the $H_2S$ content in these two bottles is evaluated by "head space" gas phase chromatography by measuring, during the storage, the height of the corresponding peak, the value of the height of the peak being arbitrary. The results obtained are given in the appended FIG. 1. In this figure, the storage time in days is placed on the abscissa and the height of the peak corresponding to $H_2S$ obtained by "head space" gas phase chromatography is placed on the ordinate. The curve (1) corresponds to the control bottle not containing a deodorizing sachet and the curve (2) to the bottle containing a deodorizing assembly according to the invention. It is observed that there is practically no $H_2S$ contained in the bottle containing the sachet; the deodorization is very efficient.

EXAMPLE 2

A deodorizing assembly consisting of a hermetically sealed, low density polyethylene sachet having a thickness of 300 µm and a surface area of 40 $cm^2$ and containing 200 mg of finely divided cuprous oxide is placed in a bottle of 33 ml capacity. 25 ml of thioglycolic acid in aqueous solution at a concentration of 92 g/l (1M) is next introduced.

The initial content of $H_2S$ and of methanethiol is measured by "head space" gas phase chromatography. The air is flushed from the bottle using a stream of nitrogen and the bottle is closed hermetically and stored at ambient temperature. At the end of 18 hours, the content of $H_2S$ and of methanethiol is measured by "head space" gas phase chromatography. The $H_2S$ content is equal to 6.5% of the initial value and the presence of methanethiol can no longer be detected. At the end of 48 hours, the pH of the solution is adjusted to a value of 9 using monoethanolamine: it then becomes possible to detect by nose the faintly ammoniacal odor of the base, which is not masked by any malodorous compound.

EXAMPLE 3

A bottle with a capacity of 60 ml is used. A deodorizing assembly consisting of a sachet of a butadiene-styrene copolymer, marketed under the trade name "STYROLUX KR 2688"0 by the company "BASF", of 40 µm in thickness and of 50 $cm^2$ surface area containing 500 mg of cuprous oxide at a concentration of 97% by weight is introduced into this bottle. 40 ml of an aqueous solution of thioglycolic acid at a concentration of 184 g/l (equivalent to 2M) is next introduced. The bottle is then sealed: it contains 20 ml of air.

The $H_2S$ content was measured by "head space" gas phase chromatography at the start, at the end of two days and at the end of 16 days. It was observed that, at the end of two days, the $H_2S$ concentration is only 19.7% of the starting concentration and that, after 16 days, it is only 0.6% of the starting concentration.

It is thus observed that, despite the presence of air in the bottle, which promotes the formation of hydrogen sulphide, the $H_2S$ content has been brought to a very low value.

EXAMPLE 4

A deodorizing assembly consisting of a sachet made of a butadiene-styrene copolymer, marketed under the trade name "STYROLUX KR 2688" by the company "BASF", of 40 μm in thickness and of 50 cm² surface area was introduced into a bottle of 60 ml capacity. The sachet contains 2.0 g of active charcoal marketed under the trade name "ACTI-CARBONE ACF3" by the company "CECA". 30 ml of an aqueous solution of thioglycolic acid at a concentration of 184 g/l (2M) is next introduced into the bottle. The bottle is sealed. It then contains 30 ml of air.

An identical bottle, but not containing a deodorizing sachet, was simultaneously prepared. The two bottles were stored at ambient temperature.

The hydrogen sulphide content was measured by "head space" gas phase chromatography. It was observed that, at the end of 3 days, the $H_2S$ content in the bottle containing the deodorizing sachet is 4.5% of that in the bottle not containing a deodorizing sachet; after storage for 10 days, this content is only 2% and after 20 days, it is only 0.1%.

EXAMPLE 5

A hermetically sealed sachet made of a butadiene-styrene copolymer marketed by the company "BASF" under the trade name "STYROLUX KR 2688", of 40 μm in thickness and of 50 cm² surface area, containing 1.5 g of a mixture of active charcoal, charcoal and cuprous oxide at a concentration of 97% by weight, the (active charcoal-charcoal/cuprous oxide) ratio by weight being 2/1, was introduced into a 60 ml bottle. 30 ml of a thioglycolic acid solution at a concentration of 184 g/l (2M) is next added. The bottle is sealed; it contains 30 ml of air.

As in the above example, an identical bottle, but not containing a deodorizing sachet, is simultaneously prepared. The two bottles are kept at ambient temperature.

The $H_2S$ content in each of the two bottles was measured by "head space" gas phase chromatography. It was observed that, at the end of 3 days, the $H_2S$ content in the bottle containing the deodorizing sachet is 7% of that in the unit not containing a deodorizing sachet, that it is only 2% at the end of 10 days and 0.15% at the end of 20 days.

EXAMPLE 6

A sachet made of low density polyethylene of 20 μm in thickness and of 50 cm² surface area containing 1.8 g of activated alumina marketed by the company "PROCATALYSE" is introduced into a bottle of 60 ml capacity. 30 ml of a thioglycolic acid solution at a concentration of 184 g/l (2M) is next introduced. The bottle is sealed; it contains approximately 30 ml of air.

As in Examples 4 and 5, a control bottle is prepared and the $H_2S$ content in the two bottles is measured after storage at ambient temperature. It is observed that, at the end of 3 days, the $H_2S$ content in the bottle containing the deodorizing sachet is only 22% of that in the control bottle, that after 10 days, it is only 2% and after 20 days it is still 2%.

EXAMPLE 7

A packaging as represented in FIG. 4 is used. The lower bottle 10 contains:

| | |
|---|---|
| Thioglycolic acid | 9.1 g |
| Water | qs 50 g |

A deodorizing sachet identical to that described in Example 1 is introduced into the bottle 10. The upper bottle 20 contains:

| | |
|---|---|
| 20% Aqueous ammonia (by weight) | 10.4 g |
| Ammonium hydrogen carbonate | 6.35 g |
| Mixture of cocoamidopropyl betaine and of glyceryl laurate sold under the trade name "TEGOBETAINE HS" by the company "GOLDSCHMIDT" in solution at an active material (AM) concentration of 30% | 0.4 g (AM) |
| Oxyethylenated oleyl alcohol containing 20 moles of ethylene oxide | 0.8 g |
| Water | qs 50 g |

The thioglycolic acid solution is mixed just at the time of use.

The user of this permanent-wave composition does not detect any unpleasant odor during its use on a head of hair.

EXAMPLE 8

A permanent reshaping reducing composition for hair is prepared by mixing the following ingredients:

| | |
|---|---|
| Thioglycolic acid | 9.1 g |
| Mixture of cocoamidopropyl betaine and of glyceryl laurate sold under the trade name "TEGOBETAINE HS" by the company "GOLDSCHMIDT" in solution at an active material (AM) concentration of 30% | 0.4 g (AM) |
| Oxyethylenated oleyl alcohol containing 20 moles of ethylene oxide | 0.8 g |
| Water | qs 100 g |

Approximately 75 ml of this solution is applied to wet hair which has been rolled onto curlers beforehand.

A cap consisting of a thin double wall made of low density polyethylene, each wall having a thickness of 20 μm and a surface area of 1300 cm² is placed on the head of hair. 2 g of a mixture consisting of 1.4 g of active charcoal sold under the trade name "AS 1544" by the company "CECA" and 0.6 g of cuprous oxide are distributed uniformly between the two walls. The cap is fitted with a securing means.

The composition is left to act for 15 minutes, after having covered the head of hair with the cap. It is observed that the cap allows unpleasant odors to be avoided during the permanent-wave reduction phase.

After rinsing copiously with water the following oxidizing composition is then applied:

| | |
|---|---|
| Hydrogen peroxide | 1.5 g |
| Oxyethylenated sodium lauryl ether sulphate containing 2 moles of ethylene oxide | 3.75 g |
| Citric acid | 0.5 g |
| Sodium hydrogen phosphate | 0.5 g |
| Perfume | 0.3 g |
| Deionized water | qs 100 g |

The oxidizing composition is left to act for approximately 5 minutes and the curlers are then removed and the hair is rinsed copiously with water. After drying under a hair dryer, the hair has beautiful curls.

I claim:

1. A method to deodorize a liquid formulation so as to remove a malodorous compound present in a liquid formulation, said method comprising providing a liquid formulation containing a compound having the formula $$HS-A-Y-B \qquad (I)$$

wherein

Y represents —COO— or —NH— and
(a) when Y represents —COO—
A represents —(CH$_2$)$_n$ wherein n is 1 or 2, or $$-\underset{R}{\underset{|}{CH}}-$$

wherein R represents linear or branched C$_1$–C$_3$ alkyl, and
B represents H, —CH$_2$—CH$_2$OH, —CH$_2$—CHOH—CH$_2$OH, $$-\underset{CH_3}{\underset{|}{CH}}-CH_2OH \quad \text{or} \quad -CH_2-\underset{OH}{\underset{|}{CH}}-CH_3, \text{ and}$$

(b) when Y represents —NH—
A represents —CH$_2$—CH$_2$— or $$-CH_2-\underset{COOR'}{\underset{|}{CH}}-$$

wherein R' represents H, methyl or ethyl,
B represents H or when A represents —CH$_2$—CH$_2$— B also represents —CO—R" wherein R" represents linear or branched C$_1$–C$_4$,
said method comprising
contacting said liquid formulation with an inert membrane which is permeable to said malodorous compound and impermeable to said compound of formula (I), and
contacting said malodorous compound having passed through said inert membrane with a physical adsorption substance having a surface area sufficient to bind said malodorous compound.

2. The method of claim 1 wherein said compound of formula (I) is selected from the group consisting of thioglycolic acid, thiolactic acid, 3-mercaptopropionic acid, glycerol monothioglycolate, glycerol 2-mercaptopropionate, an azeotropic mixture of 2-hydroxypropyl thioglycolate 2-hydroxy-1-methylethyl thioglycolate, cysteamine and an N-acylated derivative thereof, an acyl derivative containing 2 to 5 carbon atoms, cysteine, a methyl cysteinate and ethyl cysteinate.

3. The method of claim 1 wherein said inert membrane is selected from the group consisting of polytetrafluoroethylene, polyethylene, polypropylene, polystyrene and a copolymer of butadiene and styrene.

4. The method of claim 1 wherein said physical adsorption substance is selected from the group consisting of an active charcoal, a silica gel, alumina, a molecular sieve, a styrene-divinylbenzene copolymer, a styrene-ethenylbenzene copolymer and a polyphenylene oxide.

5. The method of claim 1 wherein said inert membrane forms at least one bag containing said physical adsorption substance, said bag being immersed in said liquid formulation to be deodorized.

6. The method of claim 1 wherein said physical adsorption substance is in particle form, said inert membrane comprises a covering around each of said particles, and wherein the covered particles are introduced into a receptacle containing a liquid formulation to be deodorized.

7. The method of claim 1 wherein said inert membrane and said physical adsorption substance are arranged outside a receptacle containing said liquid formulation to be deodorized, said liquid formulation and said inert membrane being contacted by a circulation device means.

8. A deodorized liquid formulation obtained by the method of claim 1.

* * * * *